(12) United States Patent
Fojtik et al.

(10) Patent No.: US 11,179,549 B2
(45) Date of Patent: Nov. 23, 2021

(54) EXOSKELETON DEVICE WITH EXPANDABLE SECTION FOR SCORING

(71) Applicant: Transit Scientific, LLC, Salt Lake City, UT (US)

(72) Inventors: Shawn P. Fojtik, Park City, UT (US); Gregory Gabay, St. Louis Park, MN (US); David Butterfield, Maple Grove, MN (US)

(73) Assignee: Transit Scientific, LLC, Salt Lake City, UT (US)

( * ) Notice: Subject to any disclaimer, the term of this patent is extended or adjusted under 35 U.S.C. 154(b) by 409 days.

(21) Appl. No.: 16/174,205

(22) Filed: Oct. 29, 2018

(65) Prior Publication Data

US 2019/0126011 A1 May 2, 2019

Related U.S. Application Data

(60) Provisional application No. 62/623,117, filed on Jan. 29, 2018, provisional application No. 62/578,378, filed on Oct. 27, 2017.

(51) Int. Cl.
*A61M 25/10* (2013.01)
*A61M 29/02* (2006.01)
(Continued)

(52) U.S. Cl.
CPC ... *A61M 25/104* (2013.01); *A61B 17/320725* (2013.01); *A61M 29/02* (2013.01);
(Continued)

(58) Field of Classification Search
CPC .......... A61F 2/013; A61F 2/958; A61F 2/915; A61F 2/95; A61F 2/07; A61M 25/104; A61M 29/02; A61B 17/320725
See application file for complete search history.

(56) References Cited

U.S. PATENT DOCUMENTS 2,854,983 A * 10/1958 Baskin .............. A61M 25/1002
604/103.11
5,336,178 A * 8/1994 Kaplan .................... A61B 8/12
604/103.01
(Continued)

FOREIGN PATENT DOCUMENTS

DE 100 17 147 A1 10/2001
JP H08502679 A 3/1996
(Continued)

OTHER PUBLICATIONS

Modern Grinding, "Hypotube Definition," http://moderngrinding.com/hypotube-definition.php (Modern Grinding, 2013).
(Continued)

*Primary Examiner* — Manuel A Mendez
(74) *Attorney, Agent, or Firm* — Dentons Durham Jones Pinegar

(57) ABSTRACT

An exoskeleton device is capable of being positioned over an expandable instrument, such as a balloon catheter. The exoskeleton device may include an expandable section that receives an expander of the expandable instrument. Expansion of the expander may cause the expandable section of the exoskeleton device to expand and force the expandable section of the exoskeleton device against a surface to be treated. The expandable section may be capable of scoring the surface against which it is forced.

20 Claims, 3 Drawing Sheets

(51) Int. Cl.
*A61B 17/3207* (2006.01)
*A61B 17/00* (2006.01)
*A61M 25/00* (2006.01)
*A61B 17/22* (2006.01)

(52) U.S. Cl.
CPC .............. *A61B 2017/00243* (2013.01); *A61B 2017/22061* (2013.01); *A61M 2025/0004* (2013.01); *A61M 2025/105* (2013.01); *A61M 2025/109* (2013.01)

(56) References Cited

U.S. PATENT DOCUMENTS

| | | | |
|---|---|---|---|
| 5,441,515 A | 8/1995 | Khosravi et al. | |
| 5,556,408 A * | 9/1996 | Farhat | A61B 17/320725 606/159 |
| 5,562,620 A | 10/1996 | Klein et al. | |
| 5,702,410 A * | 12/1997 | Klunder | A61M 25/104 606/194 |
| 5,855,563 A | 1/1999 | Kaplan et al. | |
| 6,280,411 B1 * | 8/2001 | Lennox | A61L 29/085 604/103.01 |
| 7,252,679 B2 | 8/2007 | Fischell et al. | |
| 8,518,101 B2 | 8/2013 | Dreher | |
| 9,114,031 B2 | 8/2015 | Fulton | |
| 9,277,935 B2 | 3/2016 | Fulton | |
| 2003/0050688 A1 | 3/2003 | Fischell et al. | |
| 2005/0055082 A1 | 3/2005 | Muvhar et al. | |
| 2005/0080472 A1 | 4/2005 | Atkinson et al. | |
| 2005/0080478 A1 | 4/2005 | Barongan | |
| 2005/0267596 A1 | 12/2005 | Chen et al. | |
| 2006/0259005 A1 | 11/2006 | Konstantino et al. | |
| 2006/0271093 A1 | 11/2006 | Holman et al. | |
| 2008/0221666 A1 | 9/2008 | Licata et al. | |
| 2010/0094392 A1 | 4/2010 | Nguyen et al. | |
| 2010/0211161 A1 | 8/2010 | Dreher | |
| 2011/0238154 A1 | 9/2011 | Murphy et al. | |
| 2013/0138081 A1 | 5/2013 | Stankus et al. | |
| 2013/0144328 A1 | 6/2013 | Weber et al. | |
| 2014/0058421 A1 | 2/2014 | Lupton | |
| 2014/0163594 A1 | 6/2014 | Schur et al. | |
| 2015/0157832 A1 | 6/2015 | Moelgaard-Nielsen et al. | |
| 2015/0313732 A1 | 11/2015 | Fulton | |
| 2016/0135836 A1 | 5/2016 | Fulton | |
| 2017/0065796 A1 | 3/2017 | Fojtik | |
| 2019/0126011 A1 | 5/2019 | Fojtik et al. | |

FOREIGN PATENT DOCUMENTS

| | | |
|---|---|---|
| JP | 2005503881 A | 2/2005 |
| WO | 9409845 A1 | 5/1994 |

OTHER PUBLICATIONS

International Search Report, International Patent Application No. PCT/US2016/050815, dated Dec. 1, 2016.
Written Opinion of the International Searching Authority, International Patent Application No. PCT/US2016/050815, dated Dec. 1, 2016.
International Search Report, International Patent Application No. PCT/US2018/058057, dated Jan. 18, 2019.
Written Opinion of the International Searching Authority, International Patent Application No. PCT/US2018/058057, dated Jan. 18, 2019.
USPTO as International Searching Authority, "International Search Report and Written Opinion," International Application No. PCT/US2020/046242, dated Nov. 9, 2020.
European Patent Office, "extended European search report," European Application No. 18869708.0, dated June 29, 2021.
Japan Patent Office, "Reasons for Rejection," Japanese Application No. 2020-524127, dated May 25, 2021.

* cited by examiner

EXOSKELETON DEVICE WITH EXPANDABLE SECTION FOR SCORING

CROSS-REFERENCE TO RELATED APPLICATION

Claim for the benefit of priority to the Oct. 27, 2017 filing date of U.S. Provisional Patent Application No. 62/578,378, titled ELONGATED EXOSKELETON ELEMENT FOR USE OVER ELONGATED MEDICAL INSTRUMENTS ("the '378 Provisional Application"), and the Jan. 29, 2018 filing date of U.S. Provisional Patent Application No. 62/623,117, titled ELONGATED EXOSKELETON ELEMENT FOR USE OVER ELONGATED MEDICAL INSTRUMENTS ("the '117 Provisional Application"), are hereby made pursuant to 35 U.S.C. § 119(e). The entire disclosures of the '378 Provisional Application and the '117 Provisional Application are hereby incorporated herein.

TECHNICAL FIELD

This disclosure relates generally to exoskeleton devices for use on the outer surfaces of elongated medical instruments, such as catheters and balloons (e.g., angioplasty balloons, etc.). More specifically, this disclosure relates to exoskeleton devices with expandable sections that may be expanded in a manner that enables the exoskeleton devices to score tissues, plaques, or other targets against which the expanded exoskeleton devices are forced, which may enable further treatment (e.g., with medicines, etc.) treatment of the tissues, plaques, or other targets.

RELATED ART

Percutaneous transluminal angioplasty (PTA), which is commonly referred to as balloon angioplasty or, even more simply, as angioplasty, is a commonly used minimally invasive endovascular procedure for treating vessels (e.g., arteries, veins, etc.) whose pathways have been narrowed or obstructed (i.e., stenosis of the vessels). As a non-limiting example, angioplasty is often used to surgically treat arterial atherosclerosis (i.e., the formation of plaques on the insides of arterial walls)—a common cause of stenosis. Angioplasty typically involves introducing a deflated balloon catheter to the narrowed or obstructed portion of the vessel, which may be visually confirmed by fluoroscopy, and then inflating the balloon to force the obstructed or narrowed portion of the vessel, including the atherosclerosis, outward. A stent may be placed at that site to hold the newly revascularized portion of the vessel open. Atherosclerosis or, more specifically, the atherosclerotic plaque typically remains in place following angioplasty.

Angioplasty may be accompanied by treatment with medicines, but that treatment is typically limited to drugs that are administered to the subject for a period of time after the angioplasty procedure has been conducted. As an example, medicines that prevent or treat blood clots (e.g., acetylsalicylic acid (aspirin), an antiplatelet medication (clipidogrel), etc.) may be prescribed to a patent for a period of time (e.g., three months, six months, one year, etc.) after angioplasty and stent placement.

SUMMARY

An exoskeleton device according to this disclosure is capable of use with an expandable instrument (e.g., a balloon catheter, etc.). More specifically, an expandable section of an exoskeleton device may include a lumen that can receive the expandable instrument, including an expander of the expandable instrument (e.g., a balloon of the balloon catheter, etc.). The expandable section of the exoskeleton device, or at least a portion of the expandable section, may be capable of expanding, for example, upon expansion (e.g., inflation, etc.) of the expander of the expandable instrument over which that portion of the expandable section is positioned.

In some embodiments, when the expandable section of an exoskeleton device expands, it may be capable of being forced against and scoring an adjacent surface (e.g., an inner surface of a vessel, a surface of a plaque on an inner surface of a vessel, etc.). In a specific embodiment, the expandable section may include a plurality of struts, or spines, positioned around a circumference of the expandable section. Since the struts are positioned around the circumference of the expandable section, each strut may be somewhat arcuate, but substantially flat. Each strut may extend along a length of the expandable section. As the expandable section or a portion thereof expands (e.g., under radial tension, such as an internal force applied by an expander, etc.), portions of adjacent struts may be forced apart from one another, and each strut may rotate (e.g., by up to about 90°, etc.), causing an edge or a corner thereof to be somewhat radially disposed. When in a radially disposed orientation, the edge or corner of each strut, or spine, may engage, or contact, and even score a surface against which the strut is forced.

In a specific embodiment, the expandable section may comprise or be defined from at least a portion of a body of the exoskeleton device, such as a tube (e.g., a hypotube, etc.), which may be formed from a substantially rigid material, such as a metal (e.g., stainless steel, nitinol (nickel titanium), etc.) or a polymer (e.g., polyether ether ketone (PEEK), etc.). Struts may be defined by adjacent rows of slits, with the slits of each row being offset from, or staggered relative to, the slits of an adjacent row. Each row of slits may be positioned along a generator of the expandable section (i.e., a line extending from one end of the expandable section to the other end of the expandable section, parallel to an axis of the expandable section). Each slit may overlap, or be staggered relative to, about half of one slit (if the slit is located at or near an end of the expandable section) or two slits (if the slit is located intermediately along a length of the expandable section) of an adjacent row; stated another way, the slits of an expandable section may have a so-called "brickwork" arrangement, or they may be arranged like the bricks in a so-called "running bond pattern." Such an arrangement may enable a portion of a strut to rotate (e.g., by about 45°, by about 90°, etc.) (or cause rotation of that portion of the strut) upon expansion of a portion of the expandable section on which that strut is located or placement of that strut under radial tension. Such an arrangement, along with the material or materials from which the expandable section is formed, may enable an expanded portion of the expandable section to resiliently return to its relaxed state once radial tension (e.g., from an internal force, etc.) on that portion of the expandable section is released (e.g., when pressure from an expander of an expandable instrument within the expandable section is released, etc.). Thus, there may be no need for a separate resilient element on or within the expandable section. With such an arrangement, when the expandable section is an unexpanded state, or in a relaxed state, its outer surface may be smooth or substantially smooth (accounting for discontinuities that occur as material is removed from the tube to form the slit).

The expandable section of the exoskeleton device may also carry a medicament, which may be delivered to the surface that is engaged or scored while that surface is engaged or scored. The medicament may be carried by edges of the struts, or spines, of the exoskeleton device (e.g., coated onto the edges of the struts, etc.). Such a configuration may enable the exoskeleton device to deliver the medicament to a surface upon expanding the expandable section, or a portion thereof, to cause one or more struts, or spines, of the exoskeleton device to score that surface. Alternatively, the medicament may be introduced into a lumen of the exoskeleton device in a manner that enables it to flow onto or through outer surfaces of the struts while the expandable section is in a fully expanded state (e.g., expanded to a limit defined by a vessel or other structure within which the expandable section is disposed, by a balloon or another expandable instrument within the expandable section, and/or by the expandable section itself), in a partially expanded state, or in an unexpanded state, or a relaxed state.

In addition to the expandable section, the exoskeleton device may include a distal section that is capable of introduction into a subject's body (e.g., into a vessel within the body of a subject, etc.). In some embodiments, a collar may be provided around a distal end of the exoskeleton device or around a distal end of the expandable section. The collar may comprise a smooth, even flexible member. Among other functions, the collar may facilitate introduction of the exoskeleton device into the body of a subject and/or prevent expansion of a distal end of the expandable section.

In addition, a body of the exoskeleton device may include a tubular element (e.g., an extension of the expandable section, a catheter, etc.) coextensive with a proximal end of the expandable section. The tubular element may comprise intermediate and proximal portions of the exoskeleton device. The tubular element may include a lumen that can receive an elongated medical instrument, such as an expandable instrument (e.g., a balloon catheter, etc.) and, thus, may enable placement of the exoskeleton device on the elongated medical instrument. A configuration of the tubular element may enable the tubular element and, thus, the exoskeleton device, to engage the elongated medical instrument, optionally securing the tubular element to the elongated medical instrument. The tubular element may comprise an extension of the portion of the body of the exoskeleton device from which the expandable section is formed or defined. Alternatively, the tubular element may comprise a separately manufactured structure that has been aligned with and secured to the portion of the body that forms or defines the expandable section.

In another aspect, a medical system is disclosed. A medical system according to this disclosure includes an exoskeleton device and an expandable instrument, and may also include a guide wire. The exoskeleton device may be capable of placement over the expandable instrument, or of receiving at least a portion of the expandable instrument, including an expander of the expandable instrument. Any embodiment of an exoskeleton device according to this disclosure may be included in a medical system with an expandable instrument. The expandable instrument may have any configuration suitable for the procedure to be performed using the medical system. Without limitation, the expandable instrument may comprise a balloon catheter with a configuration suitable for use in the procedure to be performed. If a guide wire is included in the medical system, it may have a size (e.g., an outer diameter) suitable for use with the selected expandable instrument and exoskeleton device.

In addition to an exoskeleton device, an expandable instrument, and an optional guide wire, a medical system may include apparatuses that facilitate introduction of the guide wire, the expandable instrument, and/or the exoskeleton device into the body of a subject (e.g., a cannula, an introducer, etc.), apparatuses that work in conjunction with the expandable instrument (e.g., a syringe or another apparatus for expanding the expander of the expandable instrument (e.g., inflating a balloon of a balloon catheter, etc.), etc.), imaging apparatuses, medicaments, and the like.

According to another aspect, methods for using an exoskeleton device are disclosed. Various embodiments of such a method include the introduction of an expandable instrument (e.g., a balloon catheter, etc.) into a subject's body. The expandable instrument may be introduced, or advanced, into the subject's body along a guide wire that was previously placed along a desired path within the subject's body. While advancing the expandable instrument into the subject's body, an expander (e.g., a balloon, etc.) of the expandable instrument may be advanced to a location within the subject's body that is to be treated (e.g., to a narrowed or occluded portion of a vessel, to a plaque in a blood vessel, to a clot, to a diseased or an injured location of a blood vessel, etc.). Advancement of the expandable instrument and its expander may be visualized or otherwise monitored in a manner known in the art (e.g., under fluoroscopy, etc.).

An exoskeleton device may be positioned over the expandable instrument. In some embodiments the exoskeleton device may be positioned over the expandable instrument before the expandable instrument is introduced and advanced into the subject's body and, thus, the exoskeleton device may be introduced and advanced into the subject's body simultaneously with introduction and advancement of the expandable instrument into the subject's body. In other embodiments, the exoskeleton device may be introduced, or advanced, into the subject's body along an expandable instrument that was previously placed along the desired path within the subject's body (e.g., by introducing the expandable instrument into a lumen of the exoskeleton device and introducing and advancing the exoskeleton device over the expandable instrument, etc.). Positioning of the exoskeleton device over the expandable instrument may include placement of an expandable section of the exoskeleton device over an expander of the expandable instrument. If necessary, the position of one or both of the expandable section of the exoskeleton device and the expander of the expandable instrument may be modified or adjusted relative to a location that is to be treated within the subject's body. As an example, the expandable section of the exoskeleton device and the expander of the expandable instrument may be moved together relative to a site that is to be treated. As another example, the expander of the expandable instrument may be moved relative to the expandable section of exoskeleton device and, optionally, relative to a treatment site within body of a subject.

With the expandable section of the exoskeleton device and the expander of the expandable instrument at desired locations within a subject's body, the expander of the expandable instrument may be expanded. Expansion of the expander of the expandable instrument may cause the expandable section of the exoskeleton device to expand. Expansion of the expandable section of the exoskeleton device may force members of the expandable section, including edges or corners of the as struts, against the location that is to be treated. As the edges or corners of the struts of the expandable section are forced against the location that is to be treated, the edges or corners of the struts of the expandable section may engage and even score that location.

Other embodiments of use of an exoskeleton device according to this disclosure may include introduction advancement of the exoskeleton device into a subject's body along a guide wire that was previously placed along a desired path within the subject's body. Advancement of the exoskeleton device may include advancement of an expandable section of the exoskeleton device to a treatment site within the subject's body (e.g., to a narrowed or occluded portion of a vessel, to a plaque in a blood vessel, to a clot, to a diseased or an injured location of a blood vessel, etc.). Advancement of the exoskeleton device and its expandable section may be visualized or otherwise monitored in a manner known in the art (e.g., under fluoroscopy, etc.).

With the exoskeleton device in place, an expandable instrument may be introduced into a lumen of the exoskeleton device and advanced into the subject's body through the exoskeleton device. Advancement of the expandable instrument may continue until an expander of the expandable instrument reaches a desired location within the expandable section of the exoskeleton device, which may be confirmed visually or in any other suitable manner known in the art (e.g., under fluoroscopy, etc.). If necessary, the position of one or both of the expandable section of the exoskeleton device and the expander of the expandable instrument may be modified or adjusted relative to a location that is to be treated within the subject's body.

In embodiments where a relatively short expander of an expandable instrument is moved and used at a plurality of different locations within a relatively long expandable section of an exoskeleton device, the relatively long expandable section may be positioned along a relatively long treatment site. The relatively short expander may be positioned at a first position along the length of the relatively long expandable section. With the relatively short expander at the first position, the relatively short expander may be expanded to cause that portion of the relatively long expandable section to expand, which may cause the edges or corners of struts of the relatively long expandable section to engage or score a first part of the relatively long treatment site. The relatively short expander may then be moved to one or more further locations along the length of the relatively long expandable section and expanded to cause the relatively long expandable section to expand at each further location, which may cause edges of corners of struts at the further location along the length of the expandable section to engage or score (a) corresponding further part(s) of the relatively long treatment site.

In embodiments where the members of the expandable section carry a medicament, the medicament may be transferred to the locations that have been engaged by the edges or corners of struts of the expandable section and introduced into any scores that have been formed at those locations. Thus, use of the exoskeleton device may direct the application of one or more medicaments to a treatment site (e.g., to the cause of a stenosis, such as an atherosclerotic plaque, etc.), and facilitate uptake of the one or more of medicaments by the treatment site.

Once the desired treatment is complete, the expander of the expandable instrument may be contracted (e.g., the balloon of a balloon catheter may be deflated, etc.), enabling the expandable section of the exoskeleton device to transition from an expanded state to an unexpanded state. The expandable section of the exoskeleton device and the expander of the expandable instrument may then be moved (e.g., advanced, withdrawn, etc.) to another treatment site. Alternatively, the exoskeleton device and the expandable instrument may be removed from the subject's body.

Other aspects of the disclosure, as well as features and advantages of various aspects of the disclosed subject matter, will become apparent to those of ordinary skill in the art through consideration of the foregoing disclosure, the accompanying drawings, and the appended claims.

DETAILED DESCRIPTION

Figure 1:
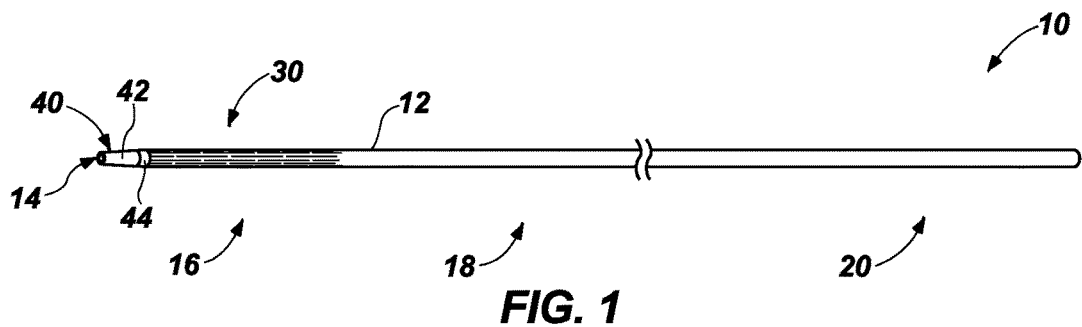
FIG. 1 illustrates an embodiment of an exoskeleton device according to this disclosure, showing an expandable section of the exoskeleton device in an unexpanded state, or a relaxed state.
Figure 2:
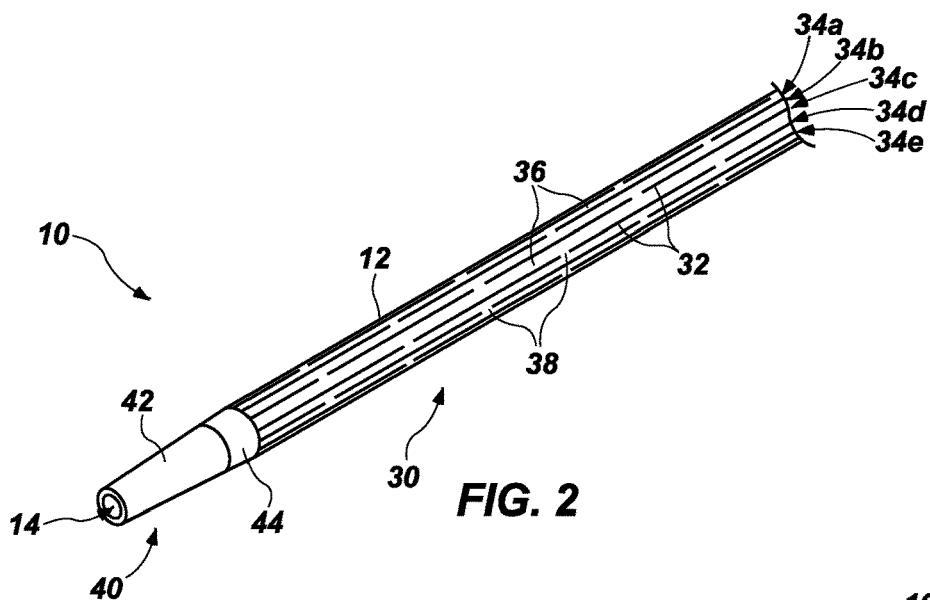
FIG. 2 provides an enlarged orthogonal view of the expandable section of embodiment of exoskeleton device shown in FIG. 1, with the expandable section in the unexpanded state.
Figure 3:
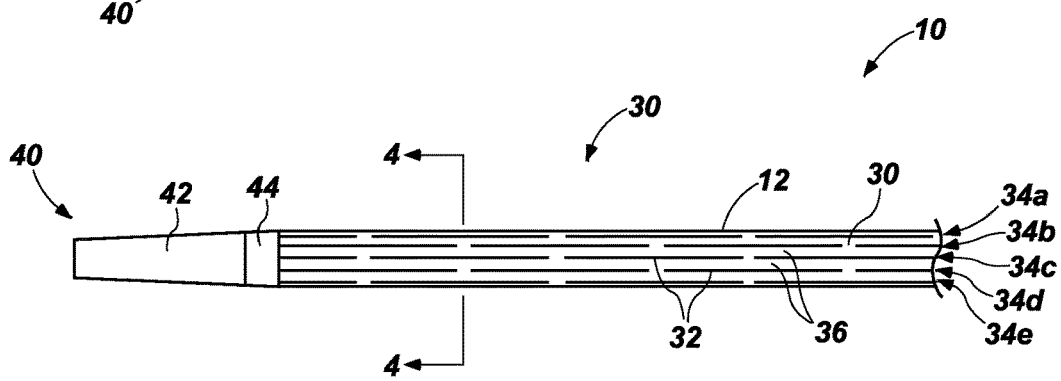
FIG. 3 provides an enlarged side view of the expandable section of the exoskeleton device in the unexpanded state.
Figure 4:
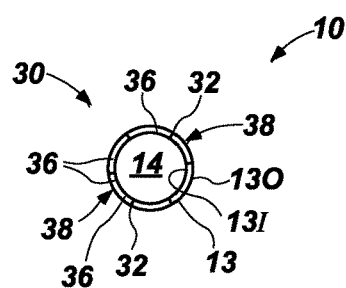
FIG. 4 provides a circumferential cross-sectional view through the expandable section in the unexpanded state, taken along line 4-4 of FIG. 3.

An embodiment of an exoskeleton device 10 according to this disclosure is depicted by FIGS. 1-8. The exoskeleton device 10 comprises an elongated medical device with an expandable section 30. The exoskeleton device 10 is at least partially defined by a body 12 that includes a distal portion 16, and intermediate portion 18, and a proximal portion 20.

At least part of the distal portion 16 of the body 12 of the exoskeleton device 10 may have a tubular configuration, through which a lumen 14 is defined. In the depicted embodiment, the body 12 has a tubular configuration along its entire length; thus, the lumen 14 extends through the entire length of the body 12.

The body 12 may comprise a substantially unitary structure or it may include a plurality of assembled elements that have been secured together. In embodiments where the body 12 includes a substantially unitary structure, it may be defined from a single element (e.g., a tube, etc.). An embodiment of the body 12 that includes a plurality of assembled elements may include a distal portion 16 that is formed separately from and subsequently assembled with and joined to a remainder of the body 12, including its intermediate portion 18 and its proximal portion 20.

The body 12 may be formed from any of a variety of suitable materials or from a combination of suitable materials. In some embodiments, the entire body 12 or its distal portion 16 may be defined from or comprise a hypotube, which may be formed from a substantially rigid material, such as a metal (e.g., stainless steel, nitinol, etc.) or a polymer (e.g., polyether ether ketone (PEEK), etc.). In embodiments where the body 12 comprises a distal portion 16 that has been formed separately from a remainder of the body 12, the remainder of the body 12 may be formed from any of a variety of suitable materials, including, without limitation, materials from which catheters may be formed (e.g., silicone, nylon, polyurethane, polyethylene, polyethylene terephthalate (PET), polytetrafluoroethylene (PTFE), latex, etc.), as well as a variety of other materials.

The expandable section 30 of the exoskeleton device 10 may be capable of expanding outward (e.g., radially outward, etc.) from an unexpanded state, as shown in FIGS. 1-4, to an expanded state, as depicted by FIGS. 5-8, upon applying an expanding force (e.g., a radially outwardly expanding force, etc.) from within the expandable section 30 to inner surfaces $13_I$ of the wall 13 of the portion of the body 12 from which the expandable section 30 is defined. The expandable section 30 may be capable of resiliently returning or substantially resiliently returning to the unexpanded state upon removal of the expanding force.

The expandable section 30 of the exoskeleton device 10 may, as illustrated, be located along the distal portion 16 of the body 12 of the exoskeleton device 10. A distal side of the expandable section 30 may be positioned adjacent to a distal end 15 of the body 12. Exoskeleton devices with expandable sections that are located at other positions (e.g. more proximal positions) along the lengths of the bodies of the exoskeleton devices (e.g., along at least part of the intermediate portion 18, along at least part of the distal portion 20, etc.) are also within the scope of this disclosure.

The expandable section 30 may comprise, or be defined by, at least part of the body 12 of the exoskeleton device 10. In the embodiment of exoskeleton device 10 illustrated by FIGS. 1 and 6, the expandable section 30 is defined by series 34a, 34b, 34c, etc., of slits 32 that extend at least partially through a wall 13 of the body 12. The slits 32 (with the exception of some slits 32 located at the ends of the expandable section 30) may have the same lengths as one another. Each slit 32 may extend radially through the wall 13 (i.e., toward a longitudinal axis 31 of the expandable section 30). In some embodiments, each slit 32 may extend completely through the wall 13 of the body 12, from its outer surface $13_O$ to its inner surface $13_I$. In other embodiments, each slit 32 may extend only partially through the wall 13 of the body 12 (e.g., from the outer surface $13_O$ of the wall 13 toward the inner surface $13_I$ of the wall 13, etc.). The extent to which each slit 32 extends through the wall 13 of the body 12 may depend, at least in part, upon the material from which the body 12 is formed. Slits 32 may be formed by any technique that is compatible with the material from which the body 12 of the exoskeleton device 10 is formed. As a non-limiting example, laser cutting processes may be used to form slits 32 in the body 12.

Each series 34a, 34b, 34c, etc., may be defined by linearly aligned slits 32. The slits 32 and each series 34a, 34b, 34c, etc., may extend longitudinally along the body 12, with each series 34a, 34b, 34c, etc., being positioned along a generator of the expandable section 30 (i.e., a line extending from one end of the expandable section 30 to the other end of the expandable section 30, parallel to the longitudinal axis 31 of the expandable section 30).

The slits 32 of each series 34b, 34c, 34d, etc., may be offset relative to the slits 32 of each adjacent series 34a, 34b, 34c, 34d, 34e, etc. Each slit 32 in a series 34a, 34b, 34c, etc., may overlap about half of one (if the slit 32 is located at or near an end of the expandable section 30) or two (if the slit 32 is intermediately located along the length of the expandable section 30) circumferentially adjacent slits 32 of each adjacent series 34a, 34b, 34c, etc. Staggering of the slits 32 around the circumference of the distal portion 16 of the body 12 of the exoskeleton device 10 may provide the expandable section 30 with a so-called "brickwork" appearance, with solid portions of the body 12 between the slits 32 arranged in a so-called "running bond pattern." In some embodiments, circumferentially corresponding slits 32 of every other series 34a and 34c, etc., of slits 32 may have equal lengths and be in complete alignment.

Circumferentially adjacent series 34a, 34b, 34c, etc., of slits 32 may be spaced equidistantly around the circumference of the body 12. The expandable section 30 may include an even number of series 34a, 34b, 34c, etc., of slits 32. In embodiments where an even number of circumferentially adjacent series 34a, 34b, 34c, etc., of slits 32 are spaced equidistantly around the circumference of the body 12, each slit 32 of the expandable section 30 may be staggered relative to its circumferentially adjacent slits 32.

The solid portions of the body 12 that are located between each adjacent pair of series 34a and 34b, 34b and 34c, 34c and 34d, etc., of slits 32 comprise struts 36 of the expandable section 30. More specifically, each strut 36 may comprise a solid portion of the body 12 between adjacent series 34a and 34b, 34b and 34c, 34c and 34d, etc., of slits 32. Solid portions of the body 12 located between adjacent slits 32 in a series 34a, 34b, 34c, etc., of slits 32 comprise joints 38 between circumferentially adjacent struts 36. Stated another way, each slit 32 comprises a gap between a pair of circumferentially adjacent struts 36.

In a specific embodiment of an exoskeleton device according to this disclosure, the body 12 may comprise a stainless steel hypotube having an outer diameter (OD) of about 0.073 inch (i.e., about 1.85 mm) and an inner diameter (ID) of about 0.067 inch (i.e., about 1.7 mm). Thus, the wall 13 of the body 12 may have a thickness of about 0.003 inch (i.e., about 0.076 mm). Twelve (12) series 34a, 34b, 34c, etc., of slits 32 may be arranged equidistantly around the circumference of the body 12, defining twelve (12) struts 36 having widths of about 0.018 inch (i.e., about 0.43 mm), accounting for the width of each slit 32. Each slit 32 may have a length of about one (1) inch (i.e., about 2.54 cm), with adjacent slits 32 in the same series 34a, 34b, 34c, etc., being spaced about 0.015 inch (i.e., about 0.38 mm) apart from each other to define joints 38 having lengths of about 0.015 inch (i.e., about 0.38 mm). Circumferentially adjacent struts 32 may be offset from one another by about half an inch (i.e., about 1.27 cm).

Figure 5:
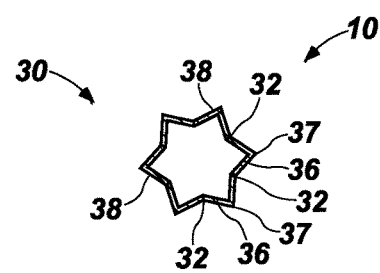
FIG. 5 is a circumferential cross-sectional representation of the expandable section of the exoskeleton device, taken transverse to a longitudinal axis of the exoskeleton device, with the expandable section in an partially expanded state.

As illustrated by FIGS. 1-4, when the expandable section 30 is in its unexpanded state, the outer surface $13_O$ of the wall 13 of the portion of the body 12 from which the expandable section 30 is defined may be substantially smooth, accounting for discontinuities that occur as material is removed from the wall 13 of the body 12 to form each slit 32. As illustrated by FIG. 5, as the expandable section 30 starts to expand, the slits 32 open up and the struts 36 may rotate from circumferentially disposed orientations (i.e., where the outer surface $13_O$ of each strut 36 is oriented along the circumference of the wall 13 of the body 12) to more radial orientations. All of the struts 36 of the expandable section 30 may rotate in the same direction (e.g., counterclockwise, clockwise, etc.). As each strut 36 begins to rotate, an edge 37 of the strut 36 is exposed at an outer extent of the expanded expandable section 30. FIG. 5 shows the expandable section 30 in a partially expanded state, or an intermediate state.

Figure 6:
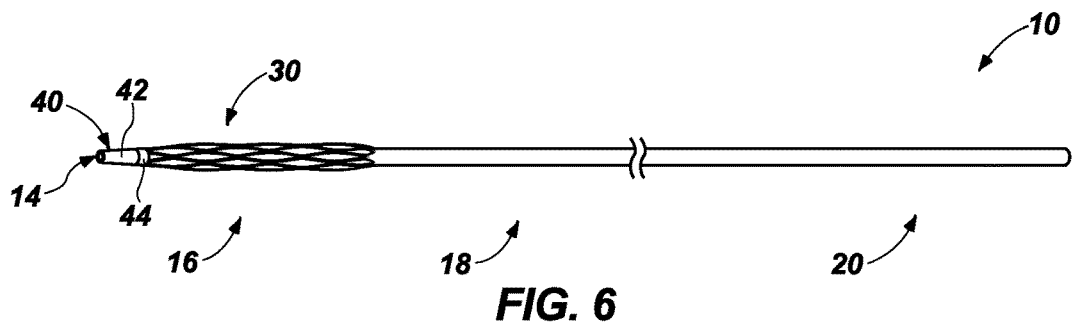
FIG. 6 illustrates the embodiment of the exoskeleton device shown in FIG. 1, showing the expandable section in an expanded state.
Figure 7:
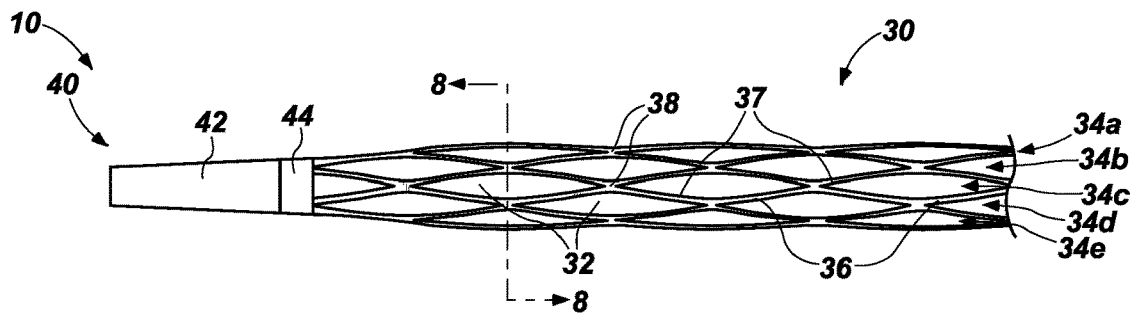
FIG. 7 provides an enlarged side view of the expandable section of the exoskeleton device in the expanded state.
Figure 8:
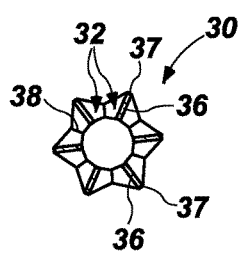
FIG. 8 provides a circumferential cross-sectional view through the expandable section in the expanded state, taken along line 8-8 of FIG. 7.

FIGS. 6-8 depict the expandable section 30 of the exoskeleton device 10 in a fully expanded state. As illustrated by FIG. 8, when the expandable section 30 is fully expanded, each strut 36 may rotate by as much as 90°, with each strut 36 being oriented substantially radially.

When the expandable section 30 is in an expanded state (i.e., partially expanded, fully expanded, etc.), the struts 36 and their at least partially outward facing edges 37 may be forced against the location that is to be treated, which may also be referred to herein as a treatment site. As the members of the expandable section are forced against the location that is to be treated, the members of the expandable section may contact that location or even score that location. In embodiments where the members of the expandable section carry a medicament, the medicament may be transferred from the struts 36 to the location that has been treated. The medicament may also be introduced into any scores formed at the location that has been treated.

With returned reference to FIGS. 1 and 6, a distal end 40 of the exoskeleton device 10 may have a configuration that enables its introduction into a subject's body (e.g., into a vessel within the body of a subject, etc.) and its advancement through the subject's body. In some embodiments, the distal end 40 of the exoskeleton device 10 may have a frustoconical configuration (i.e., it may have the shape of a truncated cone, which lacks a pointed tip). Such a configuration of distal end 40 may have a gradual taper (e.g., a taper of about 5°, a taper of about 8°, a taper of about 10°, etc.).

A collar 42 may be provided at the distal end 40 of the exoskeleton device 10 and/or at a distal side of the expandable section 30 of the exoskeleton device 10. The collar 42 may facilitate introduction of the exoskeleton device 10 into a subject's body, as well as advancement of the exoskeleton device 10 through the subject's body. Such a collar 42 may be smooth and, optionally, flexible (e.g., it may be formed from a flexible, resilient material, such as silicone, etc.). In some embodiments, the collar 42 may be provided around a distal end of the expandable section 30 to limit expansion at the distal end of the expandable section 30.

A radiopaque marker 44 may be provided at the distal end 40 of the exoskeleton device 10. The distal end 40 may be formed from a radiopaque material (e.g., platinum, etc.) to define the radiopaque marker 44, or a band of radiopaque material may be placed at or near the distal end 40 of the exoskeleton device 10 (e.g., directly adjacent to a distal side of the expandable section 30, etc.). The radiopaque marker 44 may enable visualization (e.g., through fluoroscopy, etc.) of a location of the exoskeleton device 10 and/or its expandable section 30 within a subject's body.

As illustrated by FIGS. 1 and 6, the intermediate portion 18 of the exoskeleton device 10 is located on a proximal side of the expandable section 30, and the proximal portion 20 of the exoskeleton device 10 is located on a proximal side of the intermediate portion 18, closest to an individual (e.g., a healthcare professional, etc.) introducing, advancing, and/or operating the exoskeleton device 10 and any associated devices.

The intermediate portion 18 and/or the proximal portion 20 of the exoskeleton device 10 may be capable of receiving and/or otherwise engaging one or more other elongated medical instruments (e.g., a guide wire, one or more expandable instruments, etc.) (not shown in FIGS. 1-8), including elongated medical instruments that are capable of expanding the expandable section 30 of the exoskeleton device 10 and other medical devices with which the exoskeleton device 10 may be used. In some embodiments, the intermediate portion 18 and, optionally, the proximal portion 20 of the exoskeleton device 10 may comprise a tubular element coextensive with a proximal side of the expandable section 30. The tubular element may include a lumen that can receive the one or more other elongated medical instruments. In some embodiments, the intermediate portion 18 and, optionally, the proximal portion 20 of the exoskeleton device 10 may comprise an extension of the body 12 of the exoskeleton device 10. Alternatively, the proximal portion 20 and, optionally, the intermediate portion 18 of the exoskeleton device 10 may comprise another separately manufactured structure (e.g., a catheter, another tube, a tether, etc.) that may be aligned with and is secured to a proximal end of the body 12 of the exoskeleton device 10.

Figure 9:
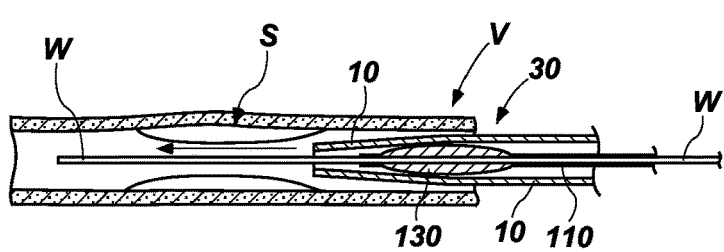
FIG. 9 is a cross-sectional representation showing an embodiment of a technique for introducing an expandable section of an exoskeleton device to a target location within a body of a subject, in which the exoskeleton device and an expandable instrument are pre-assembled with an expandable section of the exoskeleton device positioned over an expander of the expandable instrument, and then the expandable section and the expander are introduced to the target location together in an assembled relationship.
Figure 10:
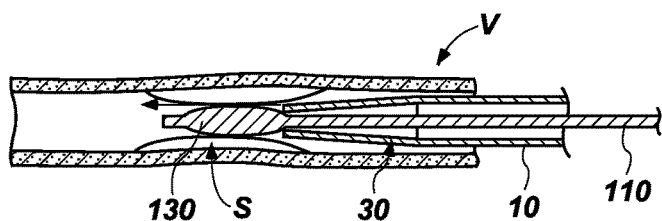
FIG. 10 is a cross-sectional representation showing another embodiment of a technique for introducing an expandable section of an exoskeleton device to a target location within a body of a subject, in which an expander of an expandable instrument is introduced to the target location, and then the exoskeleton device is introduced into the body over the expandable instrument until an expandable section of the exoskeleton device is positioned over the expander of the expandable instrument at the target location.
Figure 11:
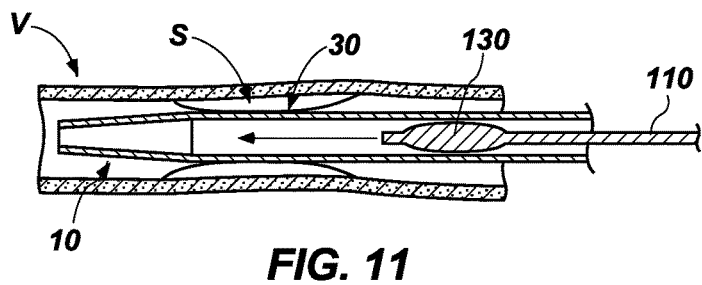
FIG. 11 is a cross-sectional representation showing yet another embodiment of a technique for introducing an expandable section of an exoskeleton device to a target location with a body of a subject, in which the exoskeleton device is introduced into the body of a subject until an expandable section of the exoskeleton device reaches a target location, and then an expandable instrument is introduced into the body through a lumen of the exoskeleton device, until an expander of the expandable instrument is positioned within the expandable section of the exoskeleton device.

Turning now to FIGS. 9-11, embodiments of various techniques for introducing an exoskeleton device 10 (FIGS. 1-8) of this disclosure into a body of a subject are depicted.

In FIG. 9, an embodiment of a technique for introducing an expandable section 30 of an exoskeleton device 10 to a treatment site S, or a target location, within a body of a subject is shown. In that method, a guide wire W is introduced into the subject's body and advanced to and, optionally, through the treatment site S in a manner known in the art. The treatment site S shown in FIG. 9 is a narrowed or occluded location along a vessel V (e.g., a blood vessel, such as an artery or a vein, etc.); it should be noted, however, that the expandable section 30 of the exoskeleton device 10 may be used to treat other organs or features of a subject's anatomy. In FIG. 9, the exoskeleton device 10 and an expandable instrument 110 are pre-assembled, with an expandable section 30 of the exoskeleton device 10 positioned over an expander 130 of the expandable instrument 110. Preassembly of the exoskeleton device 10 and the expandable instrument 110 may include securing the exoskeleton device 10 to the expandable instrument 110. The exoskeleton device 10 and the expandable instrument 110 may then be placed over the guide wire W and introduced into the subject's body together (i.e., simultaneously), and advanced along the guide wire W until the expandable section 30 and the expander 130 reach the treatment site S.

FIG. 10 illustrates another embodiment of a technique for introducing an expandable section 30 of an exoskeleton device 10 to a treatment site S within a subject's body. In the method depicted by FIG. 10, a guidewire W (FIG. 9) is first introduced into the subject's body and advanced through the subject's body to and, optionally, through the treatment site S. With the guidewire W in place, an expandable instrument 110 may then be introduced into the subject's body and advanced through the subject's body until an expander 130 at or near a distal end of the expandable instrument 110 reaches the treatment site S. With the expander 130 at the treatment site S, the guidewire W may, in some embodiments, be removed from the expandable instrument 110 and, thus, from the subject's body. The exoskeleton device 10 may be positioned over the expandable instrument 110 (e.g., a proximal end of the expandable instrument 110 may be placed in a lumen 14 (FIGS. 1 and 4) of the exoskeleton device 10, etc.) and, if the guidewire W remains in place, over the guidewire W. The exoskeleton device 10 may then be introduced into the subject's body and advanced over the expandable instrument 110, through the subject's body until the expandable section 30 is positioned over the expander 130 and at the treatment site S.

FIG. 11 depicts an embodiment of an exoskeleton device 10 introduction and advancement method that includes introducing a guidewire W (FIG. 9) into the subject's body, advanced through the subject's body to the treatment site S, and, optionally, advanced through the treatment site. With the guidewire W in place, the exoskeleton device 10 may then be introduced into the subject's body and advanced through the subject's body until an expandable section 30 of the exoskeleton device 10 reaches the treatment site S. With the expandable section 30 at the treatment site S, the guidewire W may, in some embodiments, be removed from the exoskeleton device 10 and, thus, from the subject's body. An expandable instrument 110 may be assembled with a proximal portion 20 (FIGS. 1 and 6) of the exoskeleton device 10 (e.g., introduced into a lumen 14 (FIGS. 1 and 4) of the exoskeleton device 10, etc.), and then advanced into the subject's body along the exoskeleton device 10 (e.g., through the lumen 14 of the exoskeleton device 10, etc.), until an expander 130 of the expandable instrument 110 is positioned at a desired location within the expandable section 30 of the exoskeleton device 10 and, thus, at the treatment site S.

Figure 12:
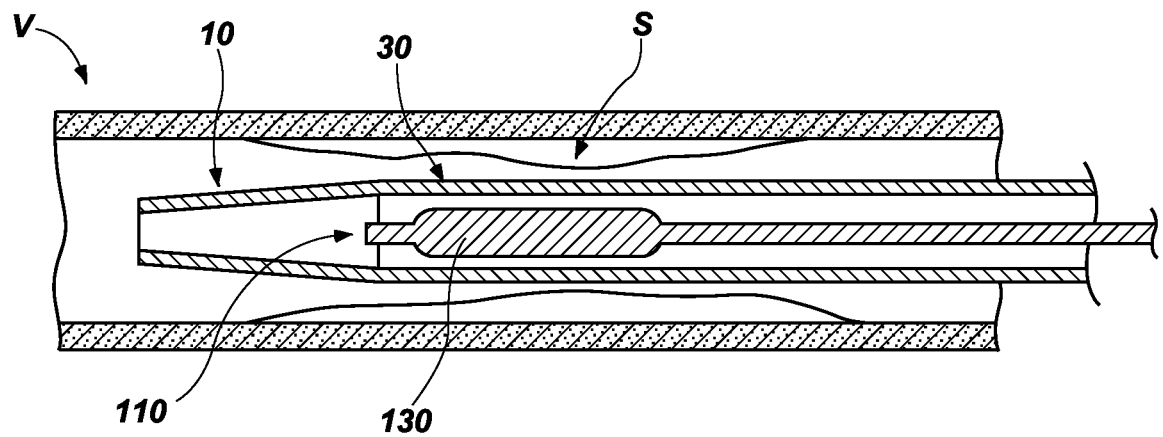
FIG. 12 is a cross-sectional representation showing an embodiment of an expander of an expandable instrument within an embodiment of an expandable section of an exoskeleton device, with the expander and the expandable section in unexpanded, or relaxed, states.
Figure 13:
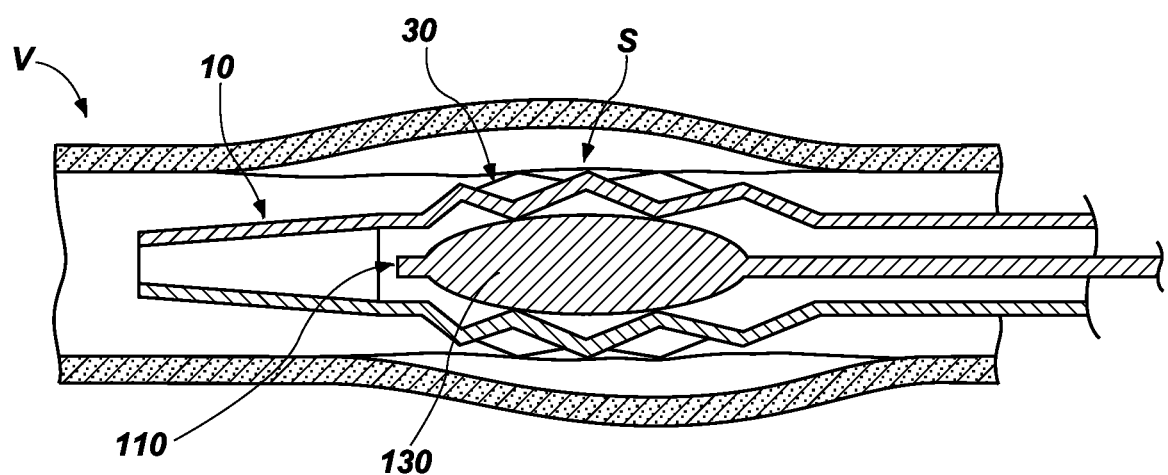
FIG. 13 is a cross sectional representation showing the embodiments of the expander and the expandable section of FIG. 12 in expanded states.

Regardless of how the expandable section 30 of the exoskeleton device 10 is introduced to the treatment site S and over the expander 130 of the expandable instrument 110, with the expandable section 30 of the exoskeleton device 10 at the treatment site S and the expander 130 of the expandable instrument 110 within the expandable section 30, as shown in FIG. 12, the expander 130 may be expanded in a suitable manner to expand the expandable section 30 (e.g., a balloon of a balloon catheter may be inflated, etc.), as illustrated by FIG. 13. With added reference to FIGS. 5 and 6-8, expansion of the expandable section 30 may cause edges 37 of the struts 36 of the expandable section 30 to contact and, optionally, score locations of the treatment site S (e.g., a diseased site, such as the site of an atherosclerotic plaque or the like; a wounded site; etc.) against which the edges 37 of the struts 36 are forced.

In embodiments such as that depicted by FIG. 11, a plurality of different expandable instruments 110 with differently configured expanders 130 (e.g., balloon catheters with balloons that expand to increasingly larger diameters, etc.) may be sequentially introduced to a treatment site S, operated (or used), and removed from the treatment site S through a single, previously placed exoskeleton device 10.

Although the foregoing description provides many specifics, these should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. An exoskeleton device capable of assembly with a balloon catheter, comprising:
   an expandable section capable of placement over an expander of an expandable instrument, the expandable section including a plurality of struts, each strut extending along a length of the expandable section with the plurality of struts being positioned around a circumference of the expandable section, each strut of the plurality of struts including a plurality of sections, each section defined by a pair of parallel slits through the expandable section, each slit of the pair of parallel slits defining the section of a strut of the plurality of struts from an adjacent section of an adjacent strut of the plurality of struts, an arrangement of slits of the expandable section rendering the expandable section radially expandable and each strut rotatable about a longitudinal axis of the strut upon radial expansion of the expandable section.

2. The exoskeleton device of claim 1, wherein an outer surface of the expandable section is substantially smooth when the expandable section is in an unexpanded state.

3. The exoskeleton device of claim 1, wherein the expandable section includes a plurality of rows of slits, each row of the plurality of rows of slits including a series of slits.

4. The exoskeleton device of claim 3, wherein the plurality of rows of slits are arranged around a circumference of the expandable section along a plurality of generators of the circumference of the expandable section.

5. The exoskeleton device of claim 3, wherein each slit of the series of slits of each row of the plurality of rows of slits is offset relative to at least one slit of the series of slits of each adjacent row of the plurality of rows of slits.

6. The exoskeleton device of claim 5, wherein each slit of the series of slits of each row of the plurality of rows of slits is offset by about half of a length of at least one slit of the series of slits of each adjacent row of the plurality of rows of slits.

7. The exoskeleton device of claim 6, wherein each slit that does not extend to an end of the expandable section has a same length as every other slit that does not extend to an end of the expandable section.

8. The exoskeleton device of claim 5, wherein slits of the series of slits of every other row of the plurality of rows of slits have equal lengths and are in complete alignment with one another.

9. An exoskeleton device capable of assembly with a balloon catheter, comprising:

an expandable section capable of being positioned over an expander of an expandable instrument, the expandable section including a plurality of slits including a plurality of rows of slits arranged around a circumference of the expandable section, each row of the plurality of rows of slits including a series of slits arranged along a generator of the circumference of the expandable section, each slit of the series of slits of each row of the plurality of rows being offset relative to at least one slit of the series of slits of each adjacent row of the plurality of rows of slits, a plurality of struts defined between each adjacent pair of rows of slits of the plurality of rows of slits and extending along a length of the expandable section, an arrangement of the plurality of slits rendering the expandable section radially expandable and each strut of the plurality of struts rotatable about a longitudinal axis of the strut upon radial expansion of the expandable section.

10. The exoskeleton device of claim 9, wherein each slit that does not extend to an end of the expandable section has a same length as every other slit that does not extend to an end of the expandable section.

11. The exoskeleton device of claim 10, wherein slits of the series of slits of every other row of the plurality of rows of slits have equal lengths and are in complete alignment with one another.

12. A medical system, comprising:

a guide wire capable of introduction into a body of a subject to define a pathway between a cutaneous location on an outside of the body and a treatment site within the body;

an exoskeleton device capable of introduction into the body and advancement through the body along the pathway, the exoskeleton device including an expandable section capable of placement at the treatment site, the expandable section including a plurality of struts capable of rotation about their longitudinal axes upon radial expansion of the expandable section; and an expandable instrument with an expander capable of introduction into the expandable section of the exoskeleton device and of causing the expandable section to expand.

13. The medical system of claim 12, wherein the plurality of struts are capable of scoring a surface against which they are forced upon expansion of the expandable section of a balloon catheter.

14. The medical system of claim 13, further comprising:
a medicament on the plurality of struts.

15. The medical system of claim 13, wherein each strut of the plurality of struts includes at least one section that is capable of being rotated upon expansion of the expandable section of the balloon catheter.

16. A method for scoring a surface within a body of a subject, comprising:

introducing an exoskeleton device into the body of a subject, with an expandable section of the exoskeleton device being introduced to a location adjacent to a surface that is to be scored;

providing an expander of an expandable instrument within the expandable section of the exoskeleton device;

expanding the expander, including causing the expandable section of the exoskeleton device to expand and struts of the expandable section to rotate about their longitudinal axes, forcing the expandable section of the exoskeleton device against the surface that is to be scored, and scoring the surface with corners or edges of the struts that have rotated to outwardly facing orientations.

17. The method of claim 16, wherein introducing the exoskeleton device into the body of the subject comprises introducing the exoskeleton device along a guide wire that has been introduced into the body of the subject.

18. The method of claim 16, wherein providing the expander of the expandable instrument within the expandable section of the exoskeleton device comprises introducing the exoskeleton device over the expandable instrument.

19. The method of claim 16, wherein providing the expander of the expandable instrument within the expandable section of the exoskeleton device comprises introducing the expandable instrument through the exoskeleton device.

20. The method of claim 16, further comprising:
introducing a medicament into scores in the surface.

* * * * *